(12) United States Patent
Reddy et al.

(10) Patent No.: US 10,053,472 B2
(45) Date of Patent: Aug. 21, 2018

(54) SILICON-BASED FUNGICIDES AND PROCESS FOR PRODUCING THE SAME

(71) Applicant: COUNCIL OF SCIENTIFIC & INDUSTRIAL RESEARCH, New Delhi (IN)

(72) Inventors: Dumbala Srinivasa Reddy, Maharashtra (IN); Gorakhnath Rajaram Jachak, Maharashtra (IN); Remya Ramesh, Maharashtra (IN); Santosh Genba Tupe, Maharashtra (IN); Mukund Vinayak Deshpande, Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 15/109,730

(22) PCT Filed: Jan. 5, 2015

(86) PCT No.: PCT/IN2015/050001
§ 371 (c)(1),
(2) Date: Jul. 5, 2016

(87) PCT Pub. No.: WO2015/102025
PCT Pub. Date: Jul. 9, 2015

(65) Prior Publication Data
US 2016/0326190 A1 Nov. 10, 2016

(30) Foreign Application Priority Data
Jan. 3, 2014 (IN) .......................... 0013/DEL/2014

(51) Int. Cl.
*C07F 7/00* (2006.01)
*C07F 7/08* (2006.01)
*A01N 55/00* (2006.01)

(52) U.S. Cl.
CPC ............ *C07F 7/0816* (2013.01); *A01N 55/00* (2013.01); *C07F 7/083* (2013.01); *C07F 7/0818* (2013.01)

(58) Field of Classification Search
CPC .................... C07F 7/08; A01N 55/00

USPC .......................................................... 556/407
See application file for complete search history.

(56) References Cited

U.S. PATENT DOCUMENTS

| 4,530,922 A | 7/1985 | Moberg |
| 4,579,842 A | 4/1986 | Acker et al. |
| 5,627,227 A * | 5/1997 | Suga ..................... C07F 7/0854 524/91 |

FOREIGN PATENT DOCUMENTS

| CA | 1086734 A | 9/1980 |
| EP | 0609099 B1 | 3/1997 |
| WO | 2006/066872 A1 | 6/2006 |
| WO | 2014/128724 A1 | 8/2014 |

OTHER PUBLICATIONS

H. Nishiyama et al., "Silicon-Directed Beckmann Fragmentation", Tetrahedron, Elsevier Science Publishers, Jan. 1, 1988, vol. 44, No. 9, pp. 2413-2426.
R. Tacke et al., "High-Affinity, Selective σ Ligands of the 1,2,3,4-Tetrahydro-1, 4'-silaspiro[naphthalene-1,4'-piperidine] Type: Synthesis, Structures, and Pharmacological Properties", ChemMedChem, Mar. 5, 2012, vol. 7, No. 3, pp. 523-532.
M. Buswell et al., "The Extraordinary Reactions of phenyldimethylsilyllithium with N,N—Disubstituted Amides", Organic & Biomolecular Chemistry, Royal Society of Chemistry, Oct. 1, 2004, vol. 2, No. 20, pp. 3006-3017.
J. Daiss et al., ".sigma. Ligands of the 1,4'-silaspirol[tetralin-1,4'-piperidine] type and the serotonin/noradrenaline reuptake inhibitor sila-venlafaxine studies on C/Si bioisosterism", Online Database Search, Chemical Abstracts Services; Retrieved from STN Database Accession No. 2008:19421.
B. Kim et al., "Diphenylsilyldiethylene-(DPSide-) Group: A New Primary Amine Protection", Online Database Search, Chemical Abstracts Service; Retrieved from STN Database Accession No. 1999:448452.

* cited by examiner

*Primary Examiner* — Clinton Brooks
*Assistant Examiner* — Kofi Adzamli
(74) *Attorney, Agent, or Firm* — Baker & Hostetler LLP

(57) ABSTRACT

The present invention discloses novel antifungal compounds of formula (I), method for preparing these compounds and the use of these compounds as antifungal agents in prevention and treatment of fungal infections, and compositions containing these novel compounds.

7 Claims, 1 Drawing Sheet

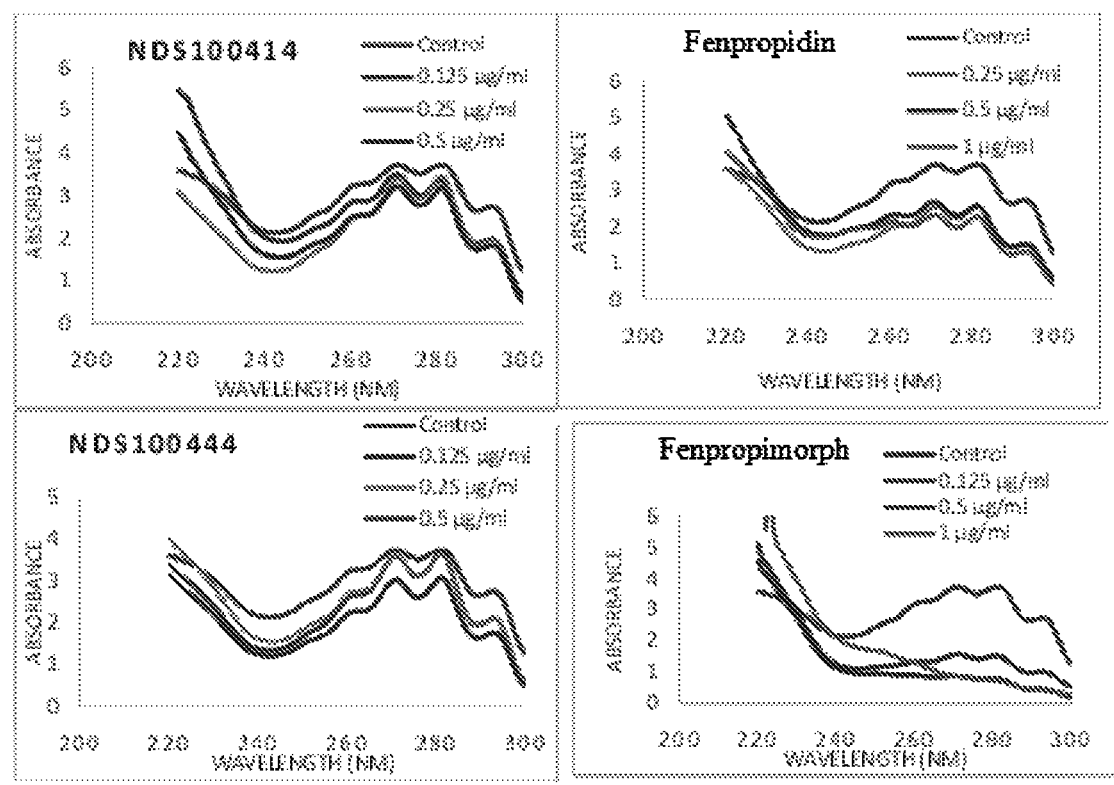

SILICON-BASED FUNGICIDES AND PROCESS FOR PRODUCING THE SAME

CROSS REFERENCE TO RELATED APPLICATIONS

This application is a National Stage of International Application No. PCT/IN2015/050001, filed on Jan. 5, 2015, which claims priority to Indian patent application no. 0013/DEL/2014, filed on Jan. 3, 2014, the disclosures of which are incorporated by reference in their entirety.

FIELD OF THE INVENTION

The present invention relates to novel silicon containing antifungal compounds of formula (I) and pharmaceutically acceptable salts thereof, and methods for preparing these compounds.

BACKGROUND AND PRIOR ART

Fungi infecting plants are evolving continuously into resistant strains, i.e. strains resistant to currently commercially available fungicides. This is of critical economic importance to farmers, grain supply and export trade and to the agrochemical industry and does negatively impact them. Fungi and other infective organisms affect all crops, not only affecting yield of crops, but also causing crop failures. It is generally opined that yield of crops up to the extent of 20% may be affected by fungal infestations to crops.

Several groups of chemical compounds as well as products derived or isolated from natural resources are commercially in use as fungicides. Other traditional techniques such as crop rotation are also continuously explored to overcome this menace. At present it costs around £200 million and takes more than ten years to develop and introduce new crop protection products. At the same time, focus is also on areas such as greater understanding of genetics and molecular biology of resistance mechanisms, molecular diagnostics for early warning of resistance development, improved risk assessment translating into guidance on doses, timings, mixtures etc.

Article titled "Synthesis and fungicidal activities of silicon-containing derivatives of 2-Aryl-3-(1H-1,2,4-triazol-1-yl)propanenitriles" by H Itoh et al. published in *Chem Pharm Bull*, 2001 July; 49(7); 909-11 reports a new series of silicon-containing derivatives of 2-aryl-3-(1H-1,2,4-triazol-1-yl)propanenitriles synthesized and evaluated for fungicidal activities against rice sheath blight and powdery mildew on cucumber. These derivatives exhibited higher efficacy than reference fungicides. CA1086734A1 discloses new and valuable morpholine derivatives and salts thereof, having a good fungicidal action, fungicides containing these compounds as active ingredients, and processes for combatting fungi with these compounds.

U.S. Pat. No. 4,530,922A discloses silicon-containing triazoles and imidazoles such as allyl[bis(4-fluorophenyl)] (1H-1,2,4-triazol-1-ylmethyl) silane, and their use in controlling fungal diseases of living plants.

U.S. Pat. No. 4,579,842A discloses novel organosilyl compounds of the general formula gi below

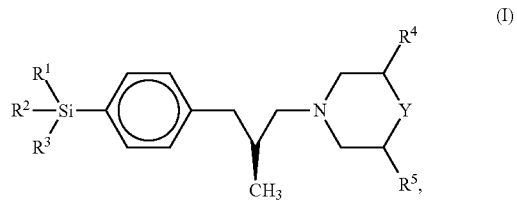

where $R^1$, $R^2$ and $R^3$ are alkyl, substituted alkyl, alkenyl, alkynyl, cycloalkyl, phenyl or substituted aryl, $R^4$ and $R^5$ are alkyl or hydrogen and Y is $CH_2$, oxygen, nitrogen or alkyl-substituted nitrogen, their salts and fungicides containing these compounds.

EP0609099B1 discloses antimicrobial and antifungal compositions for use in agriculture and horticulture, and which contain at least one 3-(1,2,4-triazol-1-yi or imidazol-1-yl)-2-hydroxy-2-(optionally substituted phenyl)-1-(trisubstituted silyl) propane derivative together with at least one further antifungal and/or antimicrobial compound.

Article titled "Short chemoenzymatic synthesis of S-enantiomers of two systemic fungicides" by M Majerić et al. published in *Biotechnology Letters*, November 1995, Volume 17, Issue 11, pp 1189-1194 reports the S-enantiomers of fenpropidine and fenpropimorph, commercially important systemic fungicides. The process comprises 2-Methyl-(4'-tert-butyl) cinnamaldehyde (1) reduced by *Saccharomyces cerevisiae* (baker's yeast) to S-3-(4'-tert-butyl)-phenyl-2-propanol (4) in high chemical and very high optical yield (e.e. ≥99%). Chlorination of 4 to 5, and alkylation of the corresponding cyclic amines complete this short enantioselective synthesis of S-1-(1'-pyperidino)-2-methyl-3-(4'tert-butyl)-phenyl-propane (6) and S-1-(1'-(3', 5'-cisdimethyl)morpholino)-2-methyl-3-(4'-tert-butyl)-phenyl-propane (7).

Therefore, an approach that may be adopted is to study the currently available options and examine as to how they may be improved or their fungicidal action enhanced. This will not only provide more alternatives to currently commercialized products, but also reduce cost and time to develop and commercialise improved options to tackle resistance.

Accordingly, the present invention provides novel antifungal agents.

OBJECTIVE OF INVENTION

The main objective of the present invention is to provide novel antifungal agents having compounds of formula (I).

Another objective of the present invention is to provide a process for preparation of novel antifungal agents having compounds of formula (I).

SUMMARY OF THE INVENTION

Accordingly, the present invention provides novel antifungal agents having compounds of formula (I);

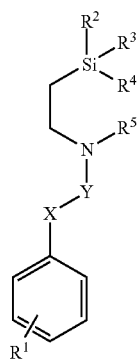

Formula - I wherein;
$R^1$ is selected from hydrogen, halogen, alkyl, haloalkyl, hydroxyalkyl, thioalkyl, $C_1$-$C_5$ alkoxy, $C_1$-$C_5$ alkoxyalkyl, —NR'R", —CH$_2$NR'R"—CONR'R", —COOR'" trialkylsilyl;
  wherein R', R" are independently hydrogen or alkyl, aryl, which may have additional substitution, or
  R' and R" together form a ring with up to six carbon atoms which optionally may be substituted and/or may contain hetero atoms;
  R'" is hydrogen or alkyl, aryl which may have additional substitution;
$R^2$, $R^3$ and $R^4$ each are individually selected from $C_1$ to $C_{12}$ alkyl, aryl, heteroaryl, aralkyl, $C_1$-$C_5$ alkoxy or any two of $R^2$, $R^3$ and $R^4$ may form 4-8 membered ring which optionally may be further substituted and/or may contain additional hetero atoms;
$R^5$ is selected from hydrogen, $C_1$ to $C_{12}$ alkyl, aryl, heteroaryl, aralkyl or $R^5$ together with any one of $R^2$, $R^3$ and $R^4$ may form a ring;
X=alkylene from $C_1$-$C_3$ which may be further substituted with alkyl, halo, haloalkyl;
Y=CO, CS, CONH, CR'R"
  wherein R' and R" are independently hydrogen or alkyl, aryl which may have additional substitution, or
  R' and R" together form a ring with up to six carbon atoms which optionally may be substituted and/or may contain hetero atoms.

In an aspect, the present invention provides a process for the preparation of compounds of formula (I) as described above.

BRIEF DESCRIPTION OF THE DRAWINGS

FIG. 1: Spectrophotometric sterol analysis of *Candida albicans* ATCC 24433 exposed with different concentrations of compounds of the present invention and reference compounds.

DETAILED DESCRIPTION OF THE INVENTION

The invention will now be described in detail in connection with certain preferred and optional embodiments, so that various aspects thereof may be more fully understood and appreciated. It should be understood, however that it is not intended to limit the invention to the particular forms/embodiments disclosed, but on the contrary, the invention is to cover all modifications, equivalents, and alternative falling within the scope of the invention as defined by the appended claims.

The following description is of exemplary embodiments only and is not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention.

The terms "comprises", "comprising", or any other variations thereof, are intended to cover a non-exclusive inclusion, such that one or more processes or composition/s or systems or methods proceeded by "comprises . . . a" does not, without more constraints, preclude the existence of other compounds, processes, sub-processes, composition, sub-compositions, minor or major compositions or other elements or other structures or additional processes or compositions or additional elements or additional features or additional characteristics or additional attributes.

In an embodiment, the present invention provides novel antifungal compounds of formula (I);

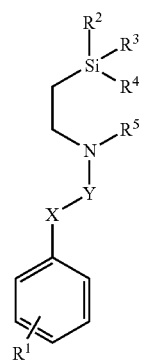

Formula (I)

or salts thereof,
wherein;
$R^1$ is selected from hydrogen, halogen, alkyl, haloalkyl, hydroxyalkyl, thioalkyl, C1-C5 alkoxy, C1-C5 alkoxyalkyl, —CH$_2$NR'R", —CONR'R", —COOR'", trialkylsilyl;
  wherein R', R" are independently hydrogen or alkyl, aryl which may have additional substitution, or
  R' and R" together form a ring with up to six carbon atoms which optionally may be substituted and/or may contain hetero atoms;
  R'" is hydrogen or alkyl, aryl which may have additional substitution;
$R^2$, $R^3$ and $R^4$ each are individually selected from $C_1$ to $C_{12}$ alkyl, aryl, heteroaryl, aralkyl, $C_1$-$C_5$ alkoxy or any two of $R^2$, $R^3$ and $R^4$ may form 4-8 membered ring which optionally may be further substituted and/or may contain additional hetero atoms;
$R^5$ is selected from hydrogen, $C_1$ to $C_{12}$ alkyl, aryl, heteroaryl, aralkyl or $R^5$ together with any one of $R^2$, $R^3$ and $R^4$ may form a ring;
X=alkylene from $C_1$-$C_3$ which may be further substituted with alkyl, halo, haloalkyl;
Y=CO, CS, CONH, CR'R";
  wherein R' and R" are independently hydrogen or alkyl, aryl which may have additional substitution, or
  R' and R" together form a ring with up to six carbon atoms which optionally may be substituted and/or may contain hetero atoms and their salts and derivatives.

The compounds of formula (I) are preferably selected from 3-(4-ter-butylphenyl-1-(4,4-dimethyl-1,4 azasilinanan-1-yl)-2-methylpropan-1-one, (R,S)1-(3-(4-(tert-butyl)phenyl)-2-methylpropyl)-4,4-dimethyl-1,4-azasilinane, 3-(4-(tert-butyl)phenyl-N-(dimethyl(phenyl)silyl)-2-methyl propanamide, 4,4-dimethyl-1-(2-methyl-3-(4-(tert-pentyl) phenyl) propyl)-1,4-azasilinane, 4,4-dimethyl-1-(2-methyl-3-(4-(trimethylsilyl) phenyl) propyl)-1,4-azasilinane.

In another embodiment, the present invention provides a process for the preparation of compounds of formula (I) comprising the steps of:
  a) adding jones reagent to a solution of (R,S)3-(4-(tert-butyl)phenyl)-2-methylpropanal (compound 1) in acetone (4 ml) at 0° C.;
  b) stirring the reaction mixture of step (a) for 6 hrs at room temperature to obtain (R,S)3-(4-(tert-butyl)phenyl)-2-methylpropanoic acid (compound 2);
  c) adding N,N-Diisopropylethylamine followed by EDC.HCl and hydroxybenzotriazole to a solution of compound 2 of step (b) and 4,4-dimethyl-1,4-azasilinane or (dimethyl(phenyl)silyl)methanamine in DCM at 0° C.;
  d) stirring the reaction mixture of step (c) for 10 hrs at room temperature to obtain desired antifungal compound of formula (I).

The process as described above may optionally further comprise the steps:
  (e) adding the compound of step (d) in THF to a suspension of lithium aluminium hydride in THF at 0° C. followed by refluxing the mixture for 4 hrs at 66° C.; and
  (f) cooling the reaction mixture of step (e) to 0° C. and excess of hydride quenched by addition of saturated aqueous sodium sulphate solution followed by stirring the reaction mixture for 3-4 hr at 25-28° C. to obtain the antifungal compound of formula (I).

In one embodiment, a composition is provided comprising a compound of formula (I), or a stereoisomer, or ester or salt thereof, and a suitable carrier, diluent or excipient.

The invention encompasses all stereoisomers and enantiomers of compounds of formula (I). The invention further encompasses pharmaceutical salts of the compound of formula (I), such as acid addition salts of mineral acids, carboxylic acids and sulfonic acids, for example salts of hydrochloric acid, hydrobromic acid, nitric acid, sulfuric acid, phosphoric acid, benzenesulfonicacid, methanesulfonic acid, ethanesulfonic acid, toluenesulfonic acid, formamidinesulfonic acid, naphthalenedisulfonic acid, formic acid, fumaric acid, acetic acid, propionic acid, lactic acid, malic acid, citric acid, maleic acid, benzoic acid, malonic acid, tartaric acid, oxalic acid and succinic acid.

The compound of formula (I) and pharmaceutical compositions containing them may be administered using any amount, any form of pharmaceutical composition via any route of administration effective for treating the disease. Typical routes of administering such pharmaceutical compositions include, without limitation, oral, topical, transdermal, inhalation, parenteral, sublingual, buccal, rectal, vaginal, and intranasal.

As used herein, the term "therapeutically effective amount" means an amount used in the pharmaceutical preparations to achieve the desired therapeutic effect. The amount/quantity of the compound used in pharmaceutical compositions of the present invention will vary depending upon the body weight of the patient and the mode of administration and can be of any effective amount to achieve the desired therapeutic effect.

In still another embodiment, the invention provides method for treating or preventing antifungal infections in a subject, wherein said method comprises administering therapeutically effective amounts of the compounds of formula (I) of the present invention or pharmaceutical composition comprising the same. The compounds of formula (I) of the present invention can also be administered optionally with other actives depending on the disease conditions.

The term "subject" as used herein may refer to plant or animal such as human.

In preferred embodiment, the fungicidal activity of compounds of formula (I) are tested against organisms, *Fusarium oxysporum* CMI 113138, *Aspergillus flavus* ATCC 11499, *Claviceps purpurea* CMI 44613, *Alternaria solani* ATCC 11785, *Ustilago maydis* PRL 1549 and *Dekkera bruxellensis* ATCC 36234 and their MIC i.e. the concentration exhibiting >90% inhibition of the growth as compared to the growth of control was determined.

In another preferred embodiment, the antifungal activity of compounds of formula (I) are tested against human fungal pathogens *Candida albicans* ATCC 24433, *C. albicans* ATCC 10231, *Candida glabrata* NCYC 388, *Candida tropicalis* ATCC 750, *Cryptococcus neoformans* ATCC 34554, *Aspergillus niger* ATCC 10578 and their MIC i.e. the concentration exhibiting >90% inhibition of the growth as compared to the growth of control was determined.

In still another preferred embodiment, compounds of formula (I) are active against *Fusarium oxysporum* CMI 113138, *Aspergillus flavus* ATCC 11499, *Claviceps purpurea* CMI 44613, *Alternaria solani* ATCC 11785, *Ustilago maydis* PRL 1549 and *Dekkera bruxellensis* ATCC 36234.

The following examples, which include preferred embodiments, will serve to illustrate the practice of this invention, it being understood that the particulars shown are by way of example and for purpose of illustrative discussion of preferred embodiments of the invention.

EXAMPLES

Example 1 (a): Synthesis of (R,S)3-(4-(tert-butyl) phenyl)-2-methylpropanoic acid (2)

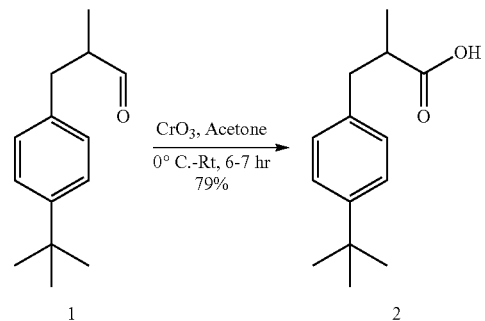 [SMILES: CC(C=O)Cc1ccc(C(C)(C)C)cc1 ; CC(Cc1ccc(C(C)(C)C)cc1)C(=O)O]

To a solution of (R,S)3-(4-(tert-butyl)phenyl)-2-methyl-propanal (1.1 g, 5.388 mmol), in acetone (4 ml) at 0° C. was added drop wise Jones reagent (377 mg $CrO_3$+0.538 ml water+0.328 ml $H_2SO_4$) and the reaction mixture was stirred at room temperature for 6 hrs. After completion of reaction, saturated sodium bisulfate was added in small portions, upper layer was decanted, and the lower layer was extracted with 90 ml of ether and combined with the original upper layer. The organic extract was washed with saturated brine solution. The organic layer was then dissolved in DCM and basified with NaHCO₃ solution, the aqueous layer was separated, cooled to 0° C. and acidified with 1N HCl. The aqueous layer was then extracted with ether, dried over Na₂SO₄ and concentrated under reduced pressure to give the product as a white solid (79% yield).

¹HNMR (200 MHz, CDCl₃): δ 7.33-7.29 (2H, d), 7.4-7.1 (2H, d), 3.08-3.02 (1H, m), 2.82-2.58 (2H, m), 1.31 (9H, s), 1.20-1.17 (3H, d)

Example 1 (b): Synthesis of 3-(4-ter-butylphenyl-1-(4,4-dimethyl-1,4 azasilinanan-1-yl)-2-methylpropan-1-one (NDS-100415)

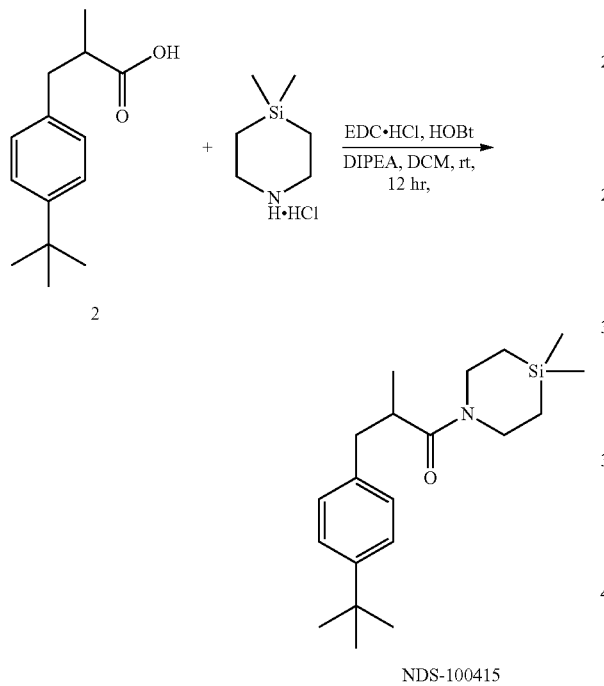

NDS-100415

To a solution of (R,S) 3-(4-(tert-butyl) phenyl)-2-methylpropanoic acid (1.2 g, 5.45 mmol) and 4,4-dimethyl-1,4-azasilinane (894 mg, 5.45 mmol) in DCM (10 mL) at 0° C., was added DIPEA (0.954 mL) followed by EDC.HCl (1.249 g, 6.54 mmol) and HOBt (882.9 mg, 6.54 mmol) and was allowed to stir at room temperature for 10 hr. The reaction mixture was diluted with DCM and washed with 1 N HCl (10 mL) followed by sat NaHCO₃ (10 mL) and brine (5 mL), dried over Na₂SO₄, concentrated under vacuum. Crude mixture was purified by silica gel column chromatography (100-200 mesh) by using ethyl acetate: pet ether (10-20%), which afforded a yellow oil as product (76% yield).

¹HNMR (400 MHz CDCl₃): δ 7.28-7.27 (d, 2H), 7.14-7.12 (d, 2H), 4.05-4.01 (m, 1H), 3.64-3.61 (m, 1H), 3.37-3.26 (m, 2H), 3.06-2.94 (m, 2H), 2.61-2.57 (m, 1H), 1.29 (s, 9H), 1.17-1.16 (d, 3H), 0.69-0.65 (m, 2H), 0.59-0.54 (m, 1H), 0.35-0.29 (m, 1H), 0.06 (s, 3H), −0.05 (s, 3H) ¹³C (100 MHz, CDCl₃): δ 174.77, 148.76, 137.49, 128.79, 125.05, 45.06, 42.28, 40.07, 37.97, 34.30, 31.36, 18.40, 15.22, 13.84, −2.56, −3.51

Example 1 (c): Synthesis of (R,S)1-(3-(4-(tert-butyl)phenyl)-2-methylpropyl)-4,4-dimethyl-1,4-azasilinane (NDS-100414)

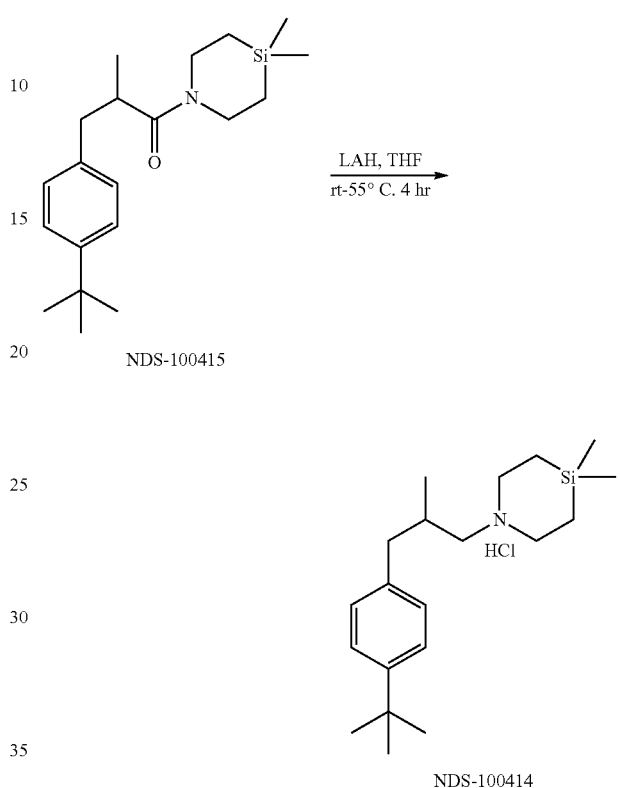

The 3-(4-ter-butylphenyl-1-(4,4-dimethyl-1,4 azasilinanan-1-yl)-2-methylpropan-1-one (600 mg, 1.812 mmol) was taken in dry THF (2 ml) and was slowly added to stirred suspension of LAH (343 mg, 9.0634 mmol) in THF (6 ml) at 0° C. and then refluxed for 4 hrs at 66° C. (monitored by TLC). It was cooled to 0° C. with ice water, the excess hydride was quenched by drop wise addition of saturated aqueous sodium sulphate solution and stirred for 3-4 hrs at room temperature (25-28° C.). White precipitate formed was filtered through celite pad, washed with EtOAc and the EtOAc layer washed with brine, dried over sodium sulphate and concentrated under vacuum to give a oily liquid. It was then dissolved in Et₂O, cooled to 0° C. and to that HCl in Et₂O was added dropwise until complete precipitation. The ether was decanted to get the pure compound as a white solid (71% yield).

¹HNMR (400 MHz CDCl₃): δ 7.34-7.32 (d, 2H), 7.12-7.10 (d, 2H), 3.4-3.39 (m, 2H), 3.2-3.11 (m, 2H), 2.97-2.92 (m, 1H), 2.75-2.70 (m, 1H), 2.65-2.59 (m, 1H), 2.56-2.51 (m, 1H), 2.17 (br, m, 1H), 1.34-1.32 (d, 3H), 1.30 (s, 9H), 1.25-1.22 (m, 1H), 1.09-1.03 (m, 1H), 0.85-0.78 (m, 1H), 0.49-0.41 (m, 1H), 0.15 (s, 3H), 0.01 (s, 3H) ¹³C (100 MHz, CDCl₃): δ 149.78, 135.87, 128.84, 125.68, 57.11, 53.44, 49.39, 41.40, 34.53, 31.45, 20.05, 8.47, 7.85, −3.26, −3.84

Example 2: Synthesis of 3-(4-(tert-butyl)phenyl-N-(dimethyl(phenyl)silyl)-2-methylpropanamide (NDS-100582)

Comparative Example

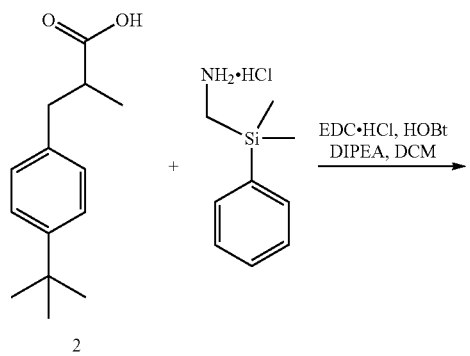

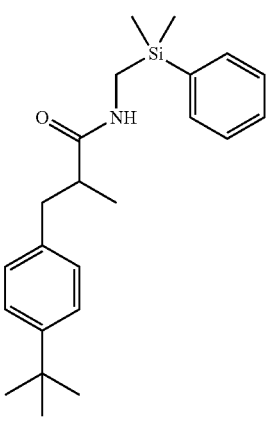

NDS-100582

The compound NDS-100582 was prepared from compound 2 and (dimethyl(phenyl)silyl)methanamine hydrochloride by following the similar procedure as mentioned for the preparation of NDS-100415. Colourless oil; 85%
$^1$H NMR (400 MHz, CDCl$_3$) δ=7.39-7.25 (m, 7H), 7.05 (m, 2H), 4.92 (brs., 1H), 2.97-2.79 (m, 3H), 2.61-2.56 (m, 1H), 2.34-2.27 (m, 1H), '1.29 (s, 9H), 1.11 (d, J=6.9 Hz, 3H), 0.23 (s, 3H), 0.16 (s, 3H). $^{13}$C NMR (100 MHz, CDCl$_3$) δ=175.6, 148.9, 136.9, 136.4, 133.6, 129.5, 128.5, 128.0, 125.3, 43.9, 39.9, 31.4, 28.4, 18.0, −4.2, −4.3.

Example 3 (a): Synthesis of 1-(4,4-dimethyl-1,4-azasilinan-1-yl)-2-methyl-3(4-tert-pentyl)phenyl) propan-1-one (compound 4)

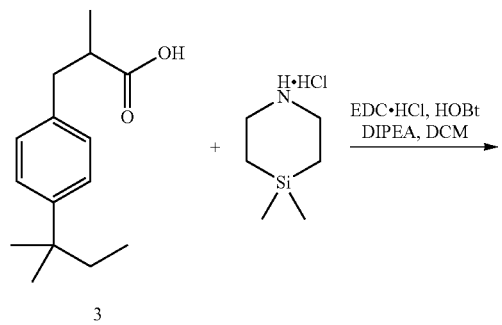

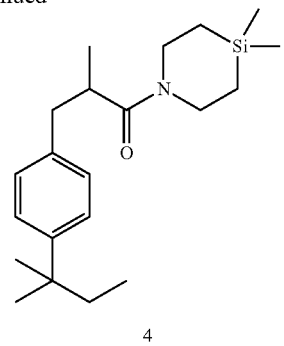

4

The compound 4 was prepared from compound 3 and 4,4-dimethyl-1,4-azasilinane hydrochloride hydrochloride by following the similar procedure as mentioned for the preparation of NDS-100415.
Colourless oil; 83% yield. $^1$HNMR (400 MHz, CDCl$_3$): δ 7.23-7.21 (d, 2H), 7.14-7.12 (d, 2H), 3.98-3.95 (m, 1H), 3.58-3.37 (m, 2H), 3.04-2.97 (m, 2H), 2.62-2.57 (m, 1H), 1.64-1.59 (d, 3H), 1.26 (s, 6H), 1.16 (d, 3H), 0.72-0.69 (t, 4H), 0.08 (s, 3H), 0.01 (s, 3H) $^{13}$C (100 MHz, CDCl$_3$): δ 174.8, 147.1, 137.3, 128.7, 125.7, 45.0, 42.2, 40.1, 37.9, 37.5, 36.8, 28.4, 18.4, 15.3, 13.8, 9.1, −2.6, −3.3.

Example 3(b): Synthesis of 4,4-dimethyl-1-(2-methyl-3-(4-(tert-pentyl)phenyl propyl)-1,4-azasilinane (NDS-100444)

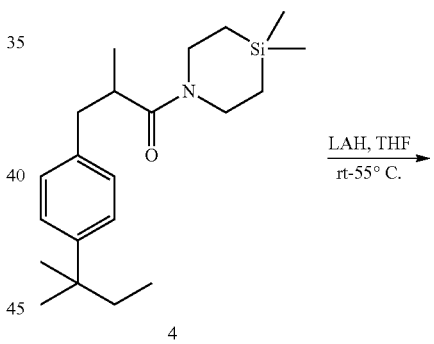

4

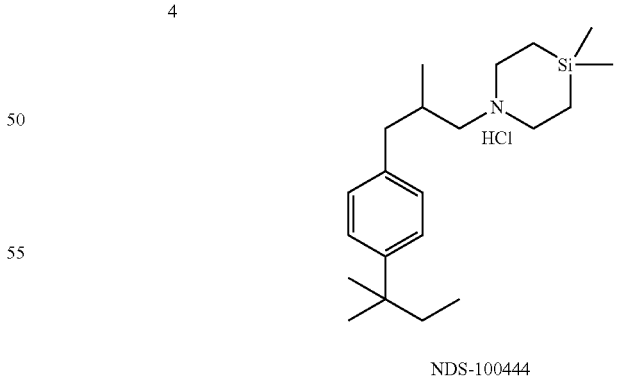

NDS-100444

The compound NDS-100444 was prepared from compound 4 by amide reduction using the same procedure as mentioned for the preparation of NDS-100414.
White solid; 80% yield. $^1$HNMR (400 MHz, CDCl$_3$): δ 7.27-7.23 (d, 2H), 7.11-7.10 (d, 2H), 3.64-3.40 (m, 2H), 3.21-3.12 (m, 2H), 3.14-3.01 (m, 2H), 2.73-2.71 (m, 1H), 2.55-2.23 (m, 3H), 1.26 (s, 6H), 1.16 (d, 3H), 0.72-0.69 (t, 4H), 0.08 (s, 3H), 0.01 (s, 3H) $^{13}$C (100 MHz, CDCl$_3$): δ 148.1, 135.6, 128.2, 126.3, 57.2, 53.5, 49.4, 41.4, 37.3, 36.8, 31.4, 30.3, 29.7, 28.5, 28.4, 20.1, 9.2, 8.5, 7.9, −3.3, −3.8.

Example 4: Synthesis of 4,4-dimethyl-1-(2-methyl-3-(4-(trimethylsilyl)phenyl) propyl)-1,4-azasilinane (NDS-100579)

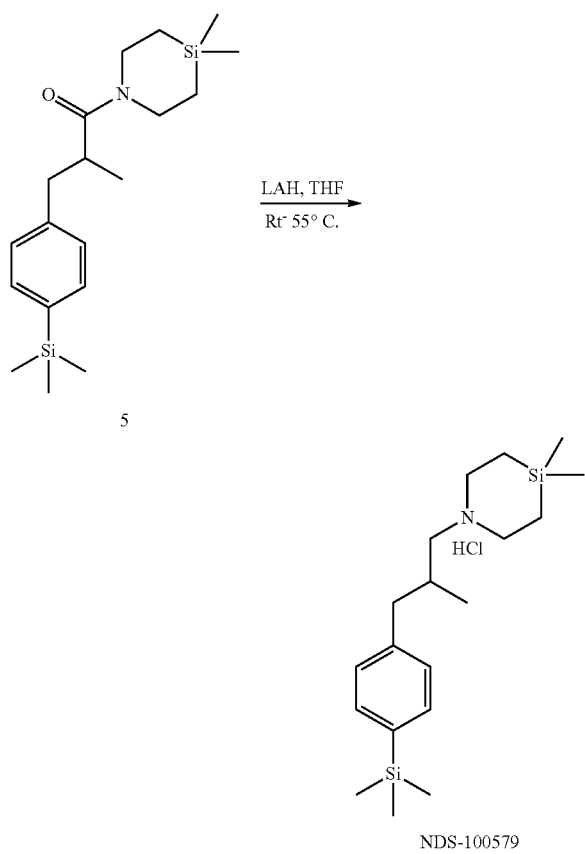

The compound 5 was prepared from 2-methyl-3-(4-(trimethylsilyl)phenyl)propanoic acid and 4,4-dimethyl-1,4-azasilinane hydrochloride by following the similar procedure as mentioned for the preparation of NDS-100415. The amide 5 was reduced using the same procedure as mentioned for the preparation of NDS-100414.

White Solid: 79%.

$^1$H NMR (400 MHz, CDCl$_3$) d=7.43 (d, J=7.6 Hz, 2H), 7.17 (d, J=7.6 Hz, 2H), 2.82 (dd, J=13.4, 4.9 Hz, 1H), 2.75-2.65 (m, 4H), 2.38-2.24 (m, 2H), 2.24-2.13 (m, 1H), 1.95-1.90 (m, 1H), 0.87 (d, J=6.2 Hz, 3H), 0.73 (t, J=6.4 Hz, 4H), 0.27 (s, 9H), 0.04 (s, 6H) $^{13}$C NMR (100 MHz, CDCl$_3$) d=142.1, 137.0, 133.1, 128.7, 63.7, 52.7, 41.5, 33.3, 18.3, 13.3, −1.0, −3.0.

Example 5: Antifungal Susceptibility Testing of Synthesized Compounds Against Plant Pathogenic Fungi In vitro antifungal assays were performed by broth microdilution method according to the Clinical and Laboratory Standards Institute (CLSI, formerly NCCL) methods M27-A3 and M-38-A2. The activity was checked against plant pathogenic fungi *Fusarium oxysporum* CMI 113138, *Aspergillus flavus* ATCC 11499, *Claviceps purpurea* CMI 44613, *Alternaria solani* ATCC 11785, *Ustilago maydis* PRL 1549 and yeast *Dekkera bruxellensis* ATCC 36234. Briefly each compound stock was prepared in DMSO at concentration of 12800 μg/ml. For assay compound stocks were serially diluted two fold in microtiter plate and 4 μl of this was used for assay to get a final concentration in the range of 256-2 μg/ml. Spores of the filamentous fungi (~2×10$^4$ spores/ml) and yeast cells freshly grown in YPG broth in logarithmic phase (~2×10$^3$ cfu/ml) were suspended in the RPMI 1640 medium and 196 μl from these were inoculated in the wells of the plate. The microtitre plate was incubated for 48-72 h. Growth was checked by visual observation and measuring absorbance at 600 nm using microtitre plate reader. The MIC was defined as the concentration exhibiting >90% inhibition of the growth as compared to the growth of control. The results are given in Table 1.

TABLE 1

Minimum Inhibitory Concentration (in μg/ml) of the compounds against plant pathogenic fungi

| Compound | *Fusarium oxysporum* CMI 113138 | *Aspergillus flavus* ATCC 11499 | *Claviceps purpurea* CMI 44613 | *Alternaria solani* ATCC 11785 | *Ustilago maydis* PRL 1549 | *Dekkera bruxellensis* ATCC 36234 |
|---|---|---|---|---|---|---|
| NDS100444 | 64 | 64 | 16 | 32 | <2 | 4 |
| NDS100414 | 64 | 128 | 4 | 32 | 32 | 16 |
| Fenpropidin (Reference Compound) | 256 | 256 | 32 | 128 | 128 | 128 |
| NDS100415 | >256 | >256 | >256 | >256 | >256 | >256 |
| Fenpropimorph_(Reference Compound) | >256 | >256 | 32 | >256 | >256 | ND |
| NDS100579 | >256 | >256 | 64 | >256 | >256 | ND |
| NDS100582 | >256 | >256 | >256 | >256 | >256 | ND |

Example 6: Antifungal Susceptibility Testing of Synthesized Compounds Against Human Pathogens Antifungal activity of the compounds was also checked against human pathogens *Candida albicans* ATCC 24433, *C. albicans* ATCC 10231, *Candida glabrata* NCYC 388, *Candida tropicalis* ATCC 750, *Cryptococcus neoformans* ATCC 34554, *Aspergillus niger* ATCC 10578, by following procedure described below. Results are given in Table 2.

TABLE 2

Minimum Inhibitory Concentration (in μg/ml) of the compounds against human fungal pathogens

| Compound | C.albicans ATCC 24433 | C.albicans ATCC 10231 | C.neoformans ATCC 34554 | C.glabrata NCYC 388 | C.tropicalis ATCC 750 | A. niger ATCC 10578 |
|---|---|---|---|---|---|---|
| NDS100444 | 4 | 0.5 | 2 | 8 | 64 | 0.5 |
| NDS100414 | 4 | 0.5 | 2 | 4 | 64 | 0.5 |
| Fenpropidin_(Reference Compound) | 0.5 | 1 | 0.5 | 0.25 | 8 | 0.5 |
| NDS100415 | >256 | >256 | >256 | >256 | >256 | >256 |
| Fenpropimorph (Reference Compound) | 0.125 | 0.25 | 0.125 | 0.125 | 4 | 1 |
| NDS100579 | 2 | 1 | 2 | 2 | 64 | 0.5 |
| NDS100582 | >256 | >256 | >256 | >256 | >256 | >256 |

From the synthesized compounds, 4 compounds NDS100414, fenpropidin, fenpropimorph and NDS100444 were found to exhibit potent antifungal activity against the tested plant and human pathogens.

Example 7: Effect of the Compounds on Sterol Composition of *C. albicans* ATCC 24433

Overnight grown culture of *C. albicans* ATCC 24433 was inoculated (106 cells/ml) in 50 ml 1% YPG broth containing 0, 0.125, 0.25, 0.50, 1, and 2 μg/ml of compounds. The flasks were incubated for 16 h with shaking at 28° C. The stationary-phase cells were harvested by centrifugation at 8000 rpm for 10 min and washed once with sterile distilled water. The net wet weight of the cell pellet was determined. To the 100 mg cell pellet, 3 ml of 25% alcoholic potassium hydroxide solution (25 g of KOH and 35 ml of sterile distilled water, brought to 100 ml with 100% ethanol), was added to each pellet and vortex mixed for 1 min. Cell suspensions were transferred to sterile borosilicate glass screw-cap tubes and were incubated in an 85° C. water bath for 1 h. Following incubation, tubes were allowed to cool to room temperature. Sterols were then extracted by addition of a mixture of 1 ml of sterile distilled water and 3 ml of n-heptane followed by vigorous vortex mixing for 3 min. The heptane layer was transferred to a clean borosilicate glass screw-cap tube and stored at −20° C. for as long as 24 h. Prior to analysis, a 20 μl aliquot of sterol extract was diluted fivefold in 100% ethanol and scanned spectrophotometrically between 220 and 300 nm on Spectrophotometer.

In sterols analysis, the presence of ergosterol and the late sterol intermediate 24(28) dehydroergosterol in a sample without any compound resulted in a characteristic four-peaked curve. In the presence of fenpropidin, fenpropimorph and derivatives NDS 100414, 100444 a dose-dependent decrease in the height of the absorbance peaks was observed and corresponded to the decrease in the ergosterol concentration in *Candida albicans* NCIM 3557 cells (FIG. 1). Results indicated that these compounds affect ergosterol synthesis pathway and results in membrane instability.

ADVANTAGES OF INVENTION

Novel compounds with improved fungicidal activity
Novel process of synthesis provided

We claim:
1. Antifungal compounds of formula (I)

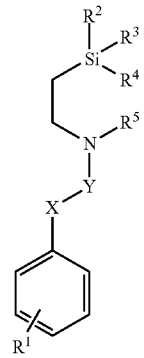

Formula (I)

or salts thereof;
wherein;
$R^1$ is selected from halogen, alkyl, haloalkyl, hydroxyalkyl, thioalkyl, $C_1$-$C_5$ alkoxyalkyl, —NR'R", —COOR'", trialkylsilyl;
wherein R', R" are independently hydrogen or alkyl, aryl, or
R' and R" together form a ring with up to six carbon atoms;
R'" is hydrogen or alkyl, aryl;
$R^2$, $R^3$ and $R^4$ each are individually selected from $C_1$ to $C_{12}$ alkyl, aryl, heteroaryl, aralkyl, $C_1$-$C_5$ alkoxy;
$R^5$ is selected from hydrogen, $C_1$ to $C_{12}$ alkyl, aryl, heteroaryl, aralkyl or R5 together with any one of $R^2$, $R^3$ and $R^4$ forming a ring;
X is alkylene selected from $C_1$-$C_3$ which is further substituted with alkyl, halo, haloalkyl;
Y is selected from CO, CS, CONH, CR'R";

wherein R' and R" are independently hydrogen or alkyl, aryl, or

R' and R" together form a ring with up to six carbon atoms.

2. The compound according to claim 1, wherein the compound is selected from 3-(4-ter-butylphenyl-1-(4, 4-dimethyl-1, 4 azasilinanan-1-yl)-2-methylpropan-1-one, (R,S) 1-(3-(4-(tert-butyl)phenyl)-2-methylpropyl)-4,4-dimethyl-1,4-azasilinane, 4,4-dimethyl-1-(2-methyl-3-(4-(tert-pentyl) phenyl)propyl)-1,4-azasilinane, 4,4-dimethyl-1-(2-methyl-3-(4-(trimethylsilyl) phenyl) propyl)-1,4-azasilinane.

3. A process for the preparation of compound of formula (I) according to claim 1, said process comprising:
(a) adding jones reagent to a solution of (R,S)3-(4-(tert-butyl)phenyl)-2-methylpropanal or compound 1 in acetone (4 ml) at 0° C.;
(b) stirring the reaction mixture of step (a) for 6 hrs at room temperature to obtain (R,S)3-(4-(tert-butyl)phenyl)-2-methylpropanoic acid or compound 2;
(c) adding N,N-Diisopropylethylamine followed by EDC.HCl and hydroxybenzotriazole to a solution of compound of step (a) and 4, 4 dimethyl-1, 4-azasilinane or (dimethyl(phenyl)silyl)methanamine in DCM at 0° C.;
(d) stirring the reaction mixture of step (c) for 10 hrs at room temperature to obtain desired antifungal compound of formula (I).

4. The process according to claim 3, further comprising
(e) adding the compound of step (d) in THF to a suspension of lithium aluminum hydride in THF at 0° C. followed by refluxing the mixture for 4 hrs at 25-28° C.; and
(f) cooling the reaction mixture of step (e) to 0° C. and excess of hydride quenched by addition of saturated aqueous sodium sulphate solution followed by stirring the reaction mixture for 3-4 hr at 25-28° C. to obtain the antifungal compound of formula (I).

5. A composition comprising antifungal compound of formula (I) according to claim 1, in combination with at least one excipient.

6. The antifungal compound of formula (I) according to claim 1 for treating fungal infection in a subject.

7. The antifungal compound of claim 6, wherein said compound of formula (I) is administered in combination with at least one pharmaceutical excipient.

* * * * *